United States Patent
Ichinokawa et al.

(10) Patent No.: US 10,703,694 B2
(45) Date of Patent: *Jul. 7, 2020

(54) METHOD OF MANUFACTURING 1-CHLORO-2,3,3-TRIFLUOROPROPENE

(71) Applicant: AGC Inc., Chiyoda-ku (JP)

(72) Inventors: Mari Ichinokawa, Chiyoda-ku (JP); Hidekazu Okamoto, Chiyoda-ku (JP); Ryuji Seki, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/251,376

(22) Filed: Jan. 18, 2019

(65) Prior Publication Data

US 2019/0152884 A1    May 23, 2019

Related U.S. Application Data

(63) Continuation of application No. 15/881,171, filed on Jan. 26, 2018, now Pat. No. 10,221,112, which is a continuation of application No. PCT/JP2016/071877, filed on Jul. 26, 2016.

(30) Foreign Application Priority Data

Jul. 27, 2015   (JP) ................................ 2015-148070

(51) Int. Cl.
  *C07C 17/25*   (2006.01)
  *C07C 21/18*   (2006.01)
  *C07B 61/00*   (2006.01)

(52) U.S. Cl.
  CPC .............. *C07C 17/25* (2013.01); *C07C 21/18* (2013.01); *C07B 61/00* (2013.01)

(58) Field of Classification Search
  CPC .......... C07C 17/25; C07C 17/16; C07C 17/42
  See application file for complete search history.

(56) References Cited

U.S. PATENT DOCUMENTS

| | | | |
|---|---|---|---|
| 5,629,461 A | 5/1997 | Yasuhara et al. | |
| 5,986,151 A | 11/1999 | Van Der Puy | |
| 10,221,112 B2 * | 3/2019 | Ichinokawa | ............ C07C 21/18 |
| 2010/0121115 A1 | 5/2010 | Rao et al. | |
| 2010/0204529 A1 | 8/2010 | Terada et al. | |
| 2011/0124930 A1 | 5/2011 | Smith et al. | |
| 2011/0319678 A1 | 12/2011 | Seki et al. | |
| 2018/0044268 A1 | 2/2018 | Karube et al. | |

FOREIGN PATENT DOCUMENTS

| | | |
|---|---|---|
| EP | 3 263 544 A1 | 1/2018 |
| JP | 60-94406 | 5/1985 |
| JP | 2-209828 A | 8/1990 |
| JP | 2010-529111 | 8/2010 |
| JP | 2011-517681 | 6/2011 |
| JP | 2013-504658 | 2/2013 |
| JP | 2016-164152 | 9/2016 |
| WO | WO 94/14737 | 7/1994 |
| WO | WO 2008/030439 A2 | 3/2008 |
| WO | WO 2009/035130 A2 | 3/2009 |
| WO | WO 2009/125199 A2 | 10/2009 |
| WO | WO 2011/031697 A2 | 3/2011 |
| WO | WO 2011/162336 A1 | 12/2011 |
| WO | WO 2016/136744 A1 | 9/2016 |

OTHER PUBLICATIONS

International Search Report dated Sep. 20, 2016 in PCT/JP2016/071877, filed on Jul. 26, 2016 (with English Translation).
Written Opinion dated Sep. 20, 2016 in PCT/JP2016/071877, filed on Jul. 26, 2016.
Zapevalov A.Y. et al.: a-a disubstituted polyfluoroalkenes, Zhurnal Organicheskoi Khimii, vol. 24, No. 8, 1988, pp. 1626-1633) (w/English abstract).

* cited by examiner

*Primary Examiner* — Jafar F Parsa

(74) *Attorney, Agent, or Firm* — Oblon, McClelland, Maier & Neustadt, L.L.P.

(57) ABSTRACT

There is provided a method of efficiently manufacturing 1-chloro-2,3,3-trifluoropropene by an industrially feasible method by using a raw material which is easy to obtain. A method of manufacturing 1-chloro-2,3,3-trifluoropropene, including subjecting 3-chloro-1,1,2,2-tetrafluoropropane to a dehydrofluorination reaction in the presence of a base.

14 Claims, No Drawings

METHOD OF MANUFACTURING 1-CHLORO-2,3,3-TRIFLUOROPROPENE

CROSS-REFERENCE TO RELATED APPLICATIONS

The present application is a continuation application of U.S. patent application Ser. No. 15/881,171 filed Jan. 26, 2018, which is a continuation of prior International Application No. PCT/JP2016/071877, filed on Jul. 26, 2016 which is based upon and claims the benefit of priority from Japanese Patent Application No. 2015-148070, filed on Jul. 27, 2015; the entire contents of all of which are incorporated herein by reference.

FIELD

The present invention relates to a method of manufacturing 1-chloro-2,3,3-trifluoropropene.

BACKGROUND 1-chloro-2,3,3-trifluoropropene (CHCl=CF—CHF$_2$. HCFO-1233 yd. hereinafter, also mentioned as 1233 yd.) is a compound which is substituted for 3,3-dichloro-1,1,1,2,2-pentafluoropropane (CF$_3$—CF$_2$—CHCl$_2$, HCFC-225ca) and 1,3-dichloro-1,1,2,2,3-pentafluoropropane (CClF$_2$—CF$_2$—CClFH, HCFC-225cb) and used for new cleaning agent, refrigerant, foaming agent, solvent, and aerosol applications which have a small global warming potential (GWP).

In this description, regarding halogenated hydrocarbon, an abbreviated name of the compound is mentioned in parentheses behind a compound name, and the abbreviated name is used instead of the compound name as necessary in this description.

In 1233 yd, a Z-isomer and an E-isomer which are geometric isomers exist according to positions of substituents on a double bond. When the compound name or the abbreviated name of the compound is used unless otherwise stated in this description, at least one type selected from the Z-isomer and the E-isomer is indicated, and when (E) or (Z) is denoted behind the compound name or the abbreviated name of the compound, an (E)-isomer or a (Z)-isomer of each compound is indicated. For example, HCFO-1233 yd(Z) indicates the Z-isomer, and HCFO-1233 yd(E) indicates the E-isomer.

As a manufacturing example of 1233 yd, an example in Patent Reference 1 (International Publication WO 1994/14737) mentions that when 3-chloro-1,1,2,2-tetrafluoropropane (CHF$_2$—CF$_2$—CH$_2$Cl. HCFC-244 ca. hereinafter, also mentioned as 244 ca.) and hydrogen fluoride are each introduced in a gas state under a nitrogen gas stream into a reaction tube made of HASTELLOY C and filled with a chromium hydroxide catalyst, a small amount of 1233 yd is by-produced with 1,1,2,2,3-pentafluoropropane (CHF$_2$—CF$_2$—CH$_2$F, HCFC-245ca).

However, the reaction mentioned in Patent Reference 1 is not suitable for mass production on an industrial scale because a conversion ratio of the raw materials is about 70%, and a production amount of 1233 yd is a by-production amount and a very small amount.

The present inventors have considered a de-HX reaction (where, X in formulas indicates Cl, I, or Br) in which a compound represented by the following formula (A) or a compound represented by the following formula (B) is used as a raw material, as another possibility of manufacturing 1233 yd.

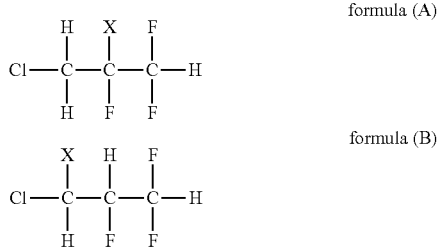

However, either of these compounds is not an easily obtainable compound, and there is not a method of industrially easily manufacturing them either, so that they are difficult to obtain. In addition, in a compound (CHF$_2$—CHF—CHFCl, HCFC-244ea) in which X is F in the formula (B), a dehydrochlorination reaction has priority over the de-HX reaction, and therefore 1233 yd cannot be selectively obtained.

SUMMARY

In the present invention, it is an object thereof to provide an economically advantageous method of efficiently manufacturing 1233 yd by an industrially feasible method by using a raw material which is easy to obtain.

The present inventors have eagerly studied a method in which as a precursor when 1233 yd is manufactured, 244 ca in which a stable manufacturing method is established is selected and 1233 yd is manufactured by subjecting the 244 ca to a dehydrofluorination reaction. As a result, they have found that employing not a gas phase reaction using activated carbon, a metal catalyst, or the like which is employed as a condition of a normal dehydrofluorination reaction but a reaction using a base makes it possible to manufacture 1233 yd selectively, and have completed the present invention.

That is, in the present invention, a method of manufacturing 1233 yd, which has the constitution indicated below, is provided.

[1] A method of manufacturing 1-chloro-2,3,3-trifluoropropene (1233 yd), the method including subjecting 3-chloro-1,1,2,2-tetrafluoropropane (244 ca) to a dehydrofluorination reaction in a presence of a base.

[2] The method of manufacturing 1233 yd according to [1], wherein the base is at least one selected from a group consisting of a metal hydroxide, a metal oxide, and a metal carbonate.

[3] The method of manufacturing 1233 yd according to [1], wherein the base is a metal hydroxide.

[4] The method of manufacturing 1233 yd according to [1], wherein the base is at least one selected from a group consisting of potassium hydroxide and sodium hydroxide.

[5] The method of manufacturing 1233 yd according to any one of [1] to [4], wherein an amount of the base is 0.5 to 10.0 mol with respect to 1 mol of the 244 ca.

[6] The method of manufacturing 1233 yd according to any one of [1] to [5], wherein the dehydrofluorination reaction is performed at a reaction temperature of 5 to 80° C.

[7] The method of manufacturing 1233 yd according to any one of [1] to [6], wherein the 244 ca is subjected to a dehydrofluorination reaction in a liquid phase in a presence of a solvent and the base.

[8] The method of manufacturing 1233 yd according to [7], wherein the solvent is water. [9] The method of manufacturing 1233 yd according to [7] or [8], wherein an amount of the base is 0.5 mass % to 48 mass % with respect to total mass of the solvent and the base.

[10] The method of manufacturing 1233 yd according to any one of [7] to [9], wherein the dehydrofluorination reaction is performed in a presence of a phase-transfer catalyst.

[11] The method of manufacturing 1233 yd according to [10], wherein the phase-transfer catalyst is a quaternary ammonium salt.

[12] The method of manufacturing 1233 yd according to [11], wherein the quaternary ammonium salt is at least one selected from a group consisting of tetra-n-butylammonium chloride, tetra-n-butylammonium bromide, and methyltri-n-octylammonium chloride.

[13] The method of manufacturing 1233 yd according to any one of [7] to [9], wherein the dehydrofluorination reaction is performed in a presence of a water-soluble organic solvent capable of dissolving the 244 ca.

[14] The method of manufacturing 1233 yd according to [13], wherein the water-soluble organic solvent is used in a proportion of 1 to 200 parts by mass to 100 parts by mass of the 244 ca.

A method of manufacturing 1233 yd of the present invention is a method of using 244 ca in which a stable manufacturing method is established and which is easy to obtain, and therefore it is a method which is easy to industrially perform and stably feasible. Further, according to the method of manufacturing 1233 yd of the present invention, it is possible to manufacture 1233 yd at a high reaction rate and with a high selectivity.

MODE FOR CARRYING OUT THE INVENTION

A method of manufacturing 1233 yd of the present invention is characterized by subjecting 244 ca to a dehydrofluorination reaction in the presence of a base. The dehydrofluorination reaction of 244 ca (hereinafter, simply also referred to as "dehydrofluorination reaction".) according to the manufacturing method of the present invention is a reaction indicated by the following formula (1).

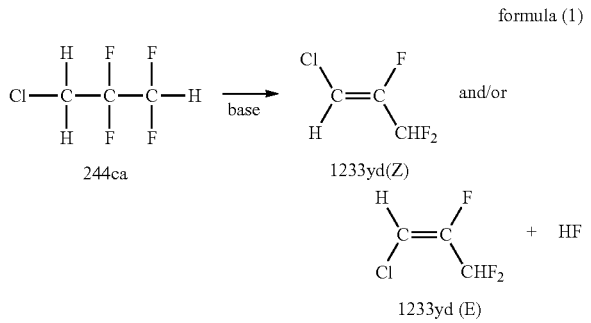

The dehydrofluorination reaction of 244 ca in the present invention can be performed by either a gas phase reaction or a liquid phase reaction, and is preferably performed by the liquid phase reaction in that its operation is more industrially advantageous. In this description, subjecting a compound (X) to the dehydrofluorination reaction by the gas phase reaction means that the compound (X) in a gaseous state is subjected to the dehydrofluorination reaction. Subjecting the compound (X) to the dehydrofluorination reaction by the liquid phase reaction means that the compound (X) in a liquid state is subjected to the dehydrofluorination reaction.

In the method of manufacturing 1233 yd of the present invention, a method of subjecting 244 ca in the liquid state to the dehydrofluorination reaction in a liquid phase is preferable from the viewpoint of a conversion ratio of 244 ca and a selectivity of 1233 yd, and the viewpoint that a size of a reactor of a reaction device can be made smaller compared with the case of performing it in a gas phase, or the like.

(244 ca)

In the method of manufacturing 1233 yd of the present invention, 244 ca is used as a raw material. 244 ca is a compound known as a production raw material or an intermediate of a fluorine-containing compound and can be easily obtained.

A method of obtaining 244 ca is not particularly limited, and for example, as indicated by a formula (2), 244 ca can be manufactured by a method of chlorinating 2,2,3,3-tetrafluoropropanol (TFPO) with thionyl chloride ($SOCl_2$) in the presence of N,N-dimethylformamide (DMF). This method can be performed in the liquid phase or in the gas phase.

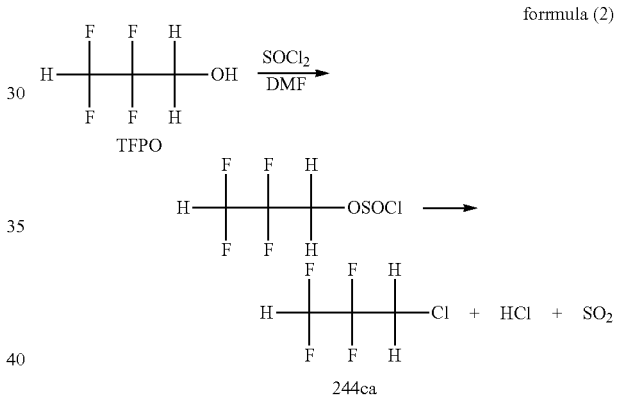

In a reaction of the formula (2), as a reactor, a commonly-used reactor, such as a glass flask, an autoclave made of SUS, and a glass-lined reactor, can be used. When the glass flask is used, it is preferable to place a glass distillation column packed with a Raschig ring and simultaneously perform production and separation of 244 ca.

It is preferable that an input amount of DMF is 0.001 to 0.2 mol and an input amount of thionyl chloride is about 0.5 to 1.5 mol with respect to 1 mol of TFPO. DMF has an action which acts in such a manner as to be a catalyst and makes the reaction progress. Because the reaction progresses quantitatively in an equimolar manner in the reaction of the formula (2), both need not be excessive.

When an addition rate of thionyl chloride with respect to 1 mol of TFPO is too fast, a production rate of hydrogen chloride increases, and there is a possibility that a product is accompanied by the hydrogen chloride and discharged to the outside of the system to be a loss. Accordingly, thionyl chloride is preferably dropped at such a rate that a temperature variation due to the reaction progress falls within 30° C. Note that when water exists, thionyl chloride is hydrolyzed by reacting with water and decomposed into $SO_2$ and HCl. Moreover, 2,2,3,3-tetrafluoropropanesulfonyl chloride is also hydrolyzed and decomposed into TFPO, $SO_2$, and HCl.

In order to prevent the above, an atmosphere in the reactor is preferably substituted for dry nitrogen gas.

In the reaction of the formula (2), TFPO and thionyl chloride react with each other by addition of the thionyl chloride to produce 2,2,3,3-tetrafluoropropanesulfonyl chloride. Heating 2,2,3,3-tetrafluoropropanesulfonyl chloride causes a de-sulfur dioxide reaction, and 244 ca is produced. A temperature at a time of the heating is 70° C. to 150° C., and preferably 90° C. to 130° C. A temperature increasing rate is optional, but in order to avoid insufficient treatment of the produced sulfur dioxide and insufficient recovery of the produced 244 ca, it is desirable to increase the temperature at a slow rate of about 1 to 2° C./min and regulate a production rate.

In the heating of 2,2,3,3-tetrafluoropropanesulfonyl chloride, when a regulation of the temperature increasing rate is difficult, it is preferable to employ a method (liquid phase reaction) of heating 2,2,3,3-tetrafluoropropanesulfonyl chloride in a solvent, for example. The solvent is a solvent whose boiling point is higher than the reaction temperature in the decomposition reaction of 2,2,3,3-tetrafluoropropanesulfonyl chloride and which does not easily react with the compounds involved in the reaction indicated by the formula (2), and an aprotic solvent is preferably used. As a specific example, dimethyl sulfoxide, DMF, or the like can be cited. A use amount of the solvent is preferably about 0.5 to 3 mol with respect to 1 mol of 2,2,3,3-tetrafluoropropanesulfonyl chloride.

A reactor similar to the one described above is prepared for the de-sulfur dioxide reaction of 2,2,3,3-tetrafluoropropanesulfonyl chloride, and the reaction is preferably performed by the liquid phase reaction. That is, when the solvent is added in the reactor and heated to a temperature at which the de-sulfur dioxide reaction is performed, 244 ca is produced by dropping 2,2,3,3-tetrafluoropropanesulfonyl chloride. The reaction temperature in the de-sulfur dioxide reaction is 70° C. to 150° C., and preferably 90° C. to 130° C. The atmosphere in the reactor is preferably substituted for the dry nitrogen gas.

A crude product of 244 ca produced through the reaction of the formula (2) is a gaseous crude product normally, and impurities are removed by performing treatment which removes hydrochloric acid and sulfur dioxide by a method such as water washing, drying the product by a drying agent such as calcium chloride or a molecular sieve, and using a method such as a cold trap, thereby allowing a composition including 244 ca to be recovered. The obtained composition including 244 ca can be used as it is or can be used, by purifying this further, for example, as a composition of 244 ca with a purity of 99.5 mass % or more, for the manufacturing method of the present invention.

As 244 ca to be used for the manufacturing method of the present invention, other than 244 ca with a purity of 100%, the composition of 244 ca with high purity which has undergone the purification process may be used, and the composition including 244 ca which include a component (for example, an impurity or the like) other than 244 ca and 244 ca may be used. However, in a case of using the latter composition including 244 ca, when the impurity is an impurity which is activated by the reaction of the present invention, it is preferably removed in advance. For example, in a case of manufacturing 244 ca by the method of the formula (2), when TFPO remains with 244 ca to be produced, TFPO sometimes reacts with 1233 yd which is the product of the present invention, and therefore TFPO is preferably removed from the product as much as possible when used in the method of the present invention.

(Base)

In the manufacturing method of the present invention, 244 ca obtained by the above method or the like is subjected to the dehydrofluorination reaction in the presence of a base. The base is not particularly limited as long as it is a base capable of carrying out the above dehydrofluorination reaction. The base preferably includes at least one type of base selected from a group constituted of a metal hydroxide, a metal oxide, and a metal carbonate.

When the base is the metal hydroxide, an alkaline-earth metal hydroxide, an alkali metal hydroxide, or the like can be cited. As the alkaline-earth metal hydroxide, for example, there can be cited magnesium hydroxide, calcium hydroxide, strontium hydroxide, or barium hydroxide. As the alkali metal hydroxide, for example, there can be cited lithium hydroxide, sodium hydroxide, or potassium hydroxide.

When the base is the metal oxide, as a metal constituting the metal oxide, there can be cited alkali metal elements, alkaline-earth metal elements, transition metal elements, group 12 metal elements, or group 13 metal elements. Among them, the alkali metal elements, the alkaline-earth metal elements, the group 6 metal elements, the group 8 metal elements, the group 10 metal elements, the group 12 metal elements, or the group 13 metal elements are preferable, and sodium, calcium, chromium, iron, zinc, or aluminum is further preferable. The metal oxide may be an oxide including one type of metal or may be a composite oxide including two or more types of metals. As the metal oxide, in terms of a reaction time and a reaction yield, sodium oxide, calcium oxide, chromium oxide (chromia), aluminum oxide (alumina), zinc oxide, or the like is preferable, and alumina and chromia are more preferable.

When the base is the metal carbonate, an alkaline-earth metal carbonate, an alkali metal carbonate, or the like can be cited. As the alkaline-earth metal carbonate, for example, there can be cited a carbonate of a metal such as beryllium, magnesium, calcium, strontium, barium, or radium. As the alkali metal carbonate, for example, there can be cited a carbonate of a metal such as lithium, sodium, potassium, rubidium, cesium, or francium.

As the base to be used for the manufacturing method of the present invention, in terms of the reaction time and the reaction yield, the metal hydroxide is preferable, and at least one selected from a group consisting of potassium hydroxide and sodium hydroxide is particularly preferable. One type of the metal hydroxide may be used alone, or two or more types may be used in combination.

A use amount of the base to be used for the manufacturing method of the present invention is preferably 0.5 to 10.0 mol, more preferably 0.5 to 5.0 mol, and further preferably 0.8 to 3.0 mol with respect to 1 mol of 244 ca from the viewpoint of the reaction yield and the selectivity of 1233 yd.

A reaction temperature of 244 ca and the base is preferably 5 to 80° C., more preferably 10 to 60° C., and further preferably 15 to 50° C. from the viewpoint of reaction activity and the selectivity of 1233 yd. When the reaction temperature does not reach the above-described range, there is a possibility of a decrease in a reaction rate and the reaction yield, and when unreacted 244 ca remains excessively, separation from 1233 yd is likely to be difficult. Further, when the reaction temperature exceeds the above-described range, there are a possibility of an increase in a production amount of 1-chloro-3,3-difluoropropyne to be produced by further dehydrofluorination of 1233 yd and a possibility of a decrease in the selectivity of 1233 yd.

When the unreacted 244 ca remains, it is also possible to concentrate 244 ca by distillation and recycle it as the raw material of the present invention.

1233 yd to be obtained in the manufacturing method of the present invention may be an E-isomer, a Z-isomer, or a mixture of these. Here, a boiling point of 244 ca is 53° C., a boiling point of 1233 yd(Z) is 54° C., and a boiling point of 1233 yd(E) is 47 to 48° C.

In the manufacturing method of the present invention, the reaction of 244 ca and the base causes the dehydrofluorination reaction (de-HF reaction) of 244 ca. In order to involve the base in the reaction, it is required to be physically in contact with 244 ca. When the manufacturing method of the present invention is performed by the gas phase reaction, a method of bringing the base in a solid, preferably, powder state and 244 ca in a gaseous state into contact with each other can be cited.

When the manufacturing method of the present invention is performed by the liquid phase reaction, a method of bringing the base dissolved in a solvent, namely, the base in a solution state and 244 ca in a liquid state into contact with each other, or the like can be cited. In these, from the viewpoint of the reaction time, the reaction yield, and the selectivity of 1233 yd, the latter liquid phase reaction is preferable. For example, a solution obtained by dissolving the base in the solvent and 244 ca are preferably brought into contact with each other by using a means such as stirring. The case of performing the manufacturing method of the present invention by the liquid phase reaction is preferable from the viewpoint that a reactor with a smaller size can be employed compared with the gas phase reaction.

As long as the solvent which can be used when the manufacturing method of the present invention is performed by the liquid phase reaction, and is used for preparing the base in the solution state is a solvent which is capable of dissolving a predetermined amount of the base and does not contribute to the dehydrofluorination reaction, it is not particularly limited. For example, as the solvent, water is preferable from the viewpoint of being capable of dissolving the alkali metal hydroxide sufficiently, having no side reaction derived from the solvent, and the like.

When the manufacturing method of the present invention is performed by the liquid phase reaction, it is preferably performed by a method in which 244 ca and the base such as the alkali metal hydroxide are subjected to the liquid phase reaction in the presence of the solvent.

In an amount of the base, in terms of the reaction rate, a proportion (unit %) of mass of the base such as the alkali metal hydroxide to a total amount (mass) of the solvent and the base is preferably an amount of 0.5 to 48 mass %, and more preferably 20 to 40 mass %. When the base amount is below the above-described range, a sufficient reaction rate cannot be sometimes obtained. On the other hand, when the base amount exceeds the above-described range, there is a possibility that the production amount of 1-chloro-3,3-difluoropropyne to be produced by a further dehydrofluorination reaction of 1233 yd increases and the selectivity of 1233 yd decreases.

When the manufacturing method of the present invention is performed as the liquid phase reaction, for the purpose of accelerating the reaction more, another substance which does not impair the effect of the present invention may be made to exist in a reaction system. For example, when as a base solution, the base solution is used by using a solvent with a high hydrophilic property, as the other substance, a phase-transfer catalyst, a water-soluble organic solvent capable of dissolving 244 ca, or the like is preferably made to exist, and the phase-transfer catalyst is particularly preferable.

As the phase-transfer catalyst, there can be cited a quaternary ammonium salt, a quaternary phosphonium salt, a quaternary arsonium salt, a sulfonium salt, crown ether, or the like, and the quaternary ammonium salt is preferable.

When the phase-transfer catalyst is the quaternary ammonium salt, a compound (hereinafter, sometimes referred to as "compound (i)") represented by the following formula (i) can be cited.

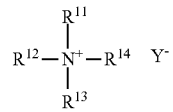

formula (i)

Where, in the formula (i), $R^{11}$ to $R^{14}$ each independently represent a monovalent hydrocarbon group or a monovalent hydrocarbon group to which a functional group inert to a reaction is bonded, and $Y^-$ represents an anion.

When $R^{11}$ to $R^{14}$ are each the hydrocarbon group, there can be cited an alkyl group, a cycloalkyl group, an alkenyl group, a cycloalkenyl group, an aryl group, or the like, and the alkyl group or the aryl group is preferable. The number of carbon atoms of $R^{11}$ to $R^{14}$ is preferably 4 to 100. $R^{11}$ to $R^{14}$ may be each the same group or may be groups different from one another. A functional group when $R^{11}$ to $R^{14}$ are each the monovalent hydrocarbon group to which a functional group inert to a reaction is bonded is appropriately selected depending on reaction conditions, but there can be cited a halogen atom, an alkoxycarbonyl group, an acyloxy group, a nitrile group, an acyl group, a carboxyl group, an alkoxyl group, or the like.

As $R^{11}R^{12}R^{13}R^{14}N^+$, N there can be cited tetramethylammonium, tetraethylammonium, tetra-n-propylammonium, tetra-n-butylammonium, methyltri-n-octylammonium, cetyltrimethylammonium, benzyltrimethylammonium, benzyltriethylammonium, cetylbenzyldimethylammonium, cetylpyridinium, n-dodecylpyridinium, phenyltrimethylammonium, phenyltriethylammonium, N-benzylpicolinium, pentamethonium, hexamethonium, or the like.

As $Y^-$, there can be cited a chlorine ion, a fluorine ion, a bromide ion, an iodine ion, a sulfate ion, a nitrate ion, a phosphate ion, a perchlorate ion, a hydrogen sulfate ion, a hydroxide ion, an acetate ion, a benzoate ion, a benzenesulfonate ion, a p-toluenesulfonate ion, or the like, and the chlorine ion, the bromide ion, the iodine ion, the hydrogen sulfate ion, or the hydroxide ion is preferable.

As the compound (i), from the viewpoint of general versatility and reactivity, combinations of the below-described $R^{11}R^{12}R^{13}R^{14}N^+$ and the below-described $Y^-$ are preferable.

$R^{11}R^{12}R^{13}R^{14}N^+$: tetramethylammonium, tetraethylammonium, tetra-n-propylammonium, tetra-n-butylammonium, or methyltri-n-octylammonium.

$Y^-$: a fluorine ion, a chlorine ion, a bromide ion, an iodine ion, or a hydroxide ion.

As the quaternary ammonium salt, tetra-n-butylammonium chloride (TBAC), tetra-n-butylammonium bromide (TBAB), or methyltri-n-octylammonium chloride (TOMAC) is preferable.

When the phase-transfer catalyst is the quaternary phosphonium salt, a compound represented by the following formula (ii) can be cited.

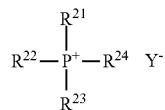

formula (ii)

Where, in the formula (ii), $R^{21}$ to $R^{24}$ each independently represent a monovalent hydrocarbon group, and $Y^-$ represents an anion.

As the hydrocarbon group in each of $R^{21}$ to $R^{24}$, there can be cited an alkyl group, a cycloalkyl group, an alkenyl group, a cycloalkenyl group, an aryl group, or the like, and the alkyl group or the aryl group is preferable.

As quaternary phosphonium ($R^{21}R^{22}R^{23}R^{24}P^+$) in the formula (ii), there can be cited tetraethylphosphonium, tetra-n-butylphosphonium, ethyltri-n-octylphosphonium, cetyltri-ethylphosphonium, cetyltri-n-butylphosphonium, n-butyltri-phenylphosphonium, n-amyltriphenylphosphonium, methyltriphenylphosphonium, benzyltriphenylphosphonium, tetraphenylphosphonium, or the like.

As $Y^-$, there can be cited a chlorine ion, a fluorine ion, a bromide ion, an iodine ion, a sulfate ion, a nitrate ion, a phosphate ion, a perchlorate ion, a hydrogen sulfate ion, a hydroxide ion, an acetate ion, a benzoate ion, a benzenesulfonate ion, a p-toluenesulfonate ion, or the like, and the fluorine ion, the chlorine ion, or the bromide ion is preferable.

When the phase-transfer catalyst is the quaternary arsonium salt, a compound represented by the following formula (iii) can be cited.

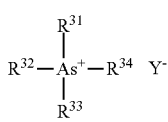

formula (iii)

Where, in the formula (iii), $R^{31}$ to $R^{34}$ each independently represent a monovalent hydrocarbon group, and $Y^-$ represents an anion.

As the hydrocarbon group in each of $R^{31}$ to $R^{34}$, for example, there can be cited an alkyl group, a cycloalkyl group, an alkenyl group, a cycloalkenyl group, an aryl group, or the like, and the alkyl group or the aryl group is preferable.

As $Y^-$, a halogen ion is preferable, and a fluorine ion, a chlorine ion, or a bromide ion is more preferable.

As the quaternary arsonium salt represented by the formula (iii), there can be cited triphenylmethylarsonium fluoride, tetraphenylarsonium fluoride, triphenylmethylarsonium chloride, tetraphenylarsonium chloride, tetraphenylarsonium bromide, or the like. As the quaternary arsonium salt, triphenylmethylarsonium chloride is particularly preferable.

When the phase-transfer catalyst is the sulfonium salt, a compound represented by the following formula (iv) can be cited.

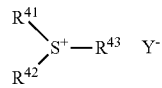

formula (iv)

Where, in the formula (iv), $R^{41}$ to $R^{43}$ each independently represent a monovalent hydrocarbon group, and $Y^-$ represents an anion.

As the hydrocarbon group in each of $R^{41}$ to $R^{43}$, for example, there can be cited an alkyl group, a cycloalkyl group, an alkenyl group, a cycloalkenyl group, an aryl group, or the like, and the alkyl group or the aryl group is preferable.

As $Y^-$, a halogen ion is preferable, and a fluorine ion, a chlorine ion, or a bromide ion is more preferable.

As the sulfonium salt represented by the formula (iv), there can be cited di-n-butylmethylsulfonium iodide, tri-n-butylsulfonium tetrafluoroborate, dihexylmethylsulfonium iodide, dicyclohexylmethylsulfonium iodide, dodecylmethylethylsulfonium chloride, tris(diethylamino)sulfonium difluorotrimethylsilicate, or the like. As the sulfonium salt, dodecylmethylethylsulfonium chloride is particularly preferable.

As the crown ether, there can be cited 18-crown-6, dibenzo-18-crown-6, dicyclohexyl-18-crown-6, or the like.

An amount of the phase-transfer catalyst is preferably 0.001 to 5 parts by mass and more preferably 0.01 to 1 parts by mass with respect to 100 parts by mass of 244 ca. When the amount of the phase-transfer catalyst is too small, a sufficient reaction rate cannot be sometimes obtained, and even though a large amount thereof is used, a reaction accelerating effect according to the use amount thereof cannot be obtained, which is disadvantageous to a cost aspect.

Further, when the reaction system separates into an aqueous phase and an organic phase, the organic phase and the aqueous phase including the base may be compatibilized by making the water-soluble organic solvent (for example, tetraglyme or the like) exist in the reaction system instead of the phase-transfer catalyst, or the phase-transfer catalyst and the water-soluble organic solvent may be used in combination.

As the water-soluble organic solvent, a solvent which is an organic solvent capable of dissolving 244 ca and has no effect on the reaction of the present invention is preferable, and tetraethylene glycol dimethyl ether (tetraglyme), sulfolane, t-butanol, or the like is preferable. The water-soluble solvent usually has compatibility with the base solution.

An amount of the water-soluble organic solvent is preferably 1 to 200 parts by mass and more preferably 10 to 100 parts by mass with respect to 100 parts by mass of 244 ca. When the amount of the water-soluble organic solvent is below the above-described range, a sufficient reaction rate cannot be sometimes obtained. Further, when the amount of the water-soluble organic solvent exceeds the above-described range, a base concentration becomes low, and therefore a reaction rate becomes small and a reaction accelerating effect according to the use amount cannot be obtained.

When the phase-transfer catalyst or the water-soluble organic solvent is used, after introduction into a reactor, it is preferable to bring the compounds involved in the reaction and these sufficiently in contact with each other by a commonly-used agitator.

The reaction in the present invention may be performed in a batch mode, or may be performed in a semi-continuous mode or a continuous flow mode. The reaction time can be appropriately regulated depending on each of the modes. As long as a material of the reactor is a material which is inert to reaction solution components including 244 ca, the phase-transfer catalyst, the water-soluble organic solvent, the base, the solvent for making this into the solution, and the reaction product, and the like and has corrosion resistance, it is not particularly limited. For example, there can be cited glass, iron, nickel, an alloy such as stainless steel containing iron or the like as a main component, and the like.

In the reaction of the present invention, 1233 yd is produced by the dehydrofluorination reaction of 244 ca, and production of 3-chloro-1,1,2-trifluoropropene (1233 yc) is also considered. However, when the manufacturing method of the present invention is performed by the liquid phase reaction, particularly when it is performed by using an aqueous solution of the alkali metal hydroxide as the base, there is the advantage that 1233 yc is hardly produced and 1233 yd can be selectively obtained.

When the manufacturing method of the present invention is performed by the liquid phase reaction, a reaction solution is left as it is after a reaction completion, thereby separating it into an organic phase and an aqueous phase. In the organic phase, other than 1233 yd which is an object, unreacted 244 ca, 1-chloro-3,3-difluoropropyne to be produced by further dehydrofluorination of 1233 yd, and the like can be included. In recovering 1233 yd from the organic phase including these, a separation and purification method by ordinary distillation or the like is preferably employed. Here, when 1233 yd(Z) is included in a product, the boiling points of 244 ca and 1233 yd(Z) are close to each other, and therefore it is preferable to perform highly accurate distillation. Further, separation of an E-isomer and a Z-isomer of 1233 yd may be performed by the separation and purification method such as the distillation in order to increase a yield of 1233 yd(Z).

By recovering 1233 yd obtained by the manufacturing method of the present invention by the separation and purification as described above, purified 1233 yd containing 1233 yd at a high purity can be obtained. When the purified 1233 yd obtained in such a manner includes acid content such as HCl, water, or oxygen, there is the possibility of corrosion of equipment in using it, a decrease in stability of 1233 yd, or the like. Accordingly, the acid content, namely, a content of the chlorine ion and the fluorine ion is preferably less than 10 mass ppm, more preferably less than 1 mass ppm, and most preferably less than 0.1 mass ppm with respect to a total amount of the purified 1233 yd. Further, a moisture concentration in the purified 1233 yd is preferably less than 1000 mass ppm, and most preferably less than 100 mass ppm. An oxygen concentration in the purified 1233 yd is preferably 1000 mass ppm or less, and more preferably 500 mass ppm or less. When the above-described ranges are beyond them, there is a possibility that decomposition of 1233 yd occurs or degreasing-cleaning ability is inhibited.

According to the manufacturing method of the present invention, performing the reaction without using special operation and reaction device by using 244 ca which can be easily obtained and stably supplied makes it possible to manufacture 1233 yd at a high reaction rate and with a high selectivity. Moreover, when the reaction by the manufacturing method of the present invention is performed by the liquid phase reaction, it is possible to reduce the reactor size in a case of manufacturing the same amount of 1233 yd compared with the gas phase reaction. That is, according to the present invention, it is possible to drastically reduce a cost required for the raw material and manufacturing facilities.

EXAMPLES

Hereinafter, the present invention will be specifically explained by examples, but the present invention is not limited by these examples.

[Condition of Gas Chromatography]

In production of the following various compounds, a chemical composition analysis of an obtained reaction composition was performed by using a gas chromatography (GC). DB-1301 (60 m in length×250 μm in inside diameter×1 μm in thickness, manufactured by Agilent Technologies, Inc.) was used as a column.

Production Example 1 of 244 ca 244 ca was produced by the following method. The following method is a method of obtaining 244 ca by chlorinating TFPO with thionyl chloride as illustrated in the formula (2).

<Synthesis of 244 ca>

In a two-liter four-necked flask with an agitator, a Dimroth condenser, and a glass distillation column (a measured value of five stages in the number of stages) packed with Raschig ring, 1204 g (9.12 mol) of TFPO and 12 g (0.17 mol) of N,N-dimethylformamide (DMF) were added. Into there, 1078 g (0.12 mol) of thionyl chloride was dropped and stirred at room temperature for 12 hours. Thereafter, a reactor was heated to 100° C., and reactive distillation was performed at a ratio of 5/1 of reflux time/distillation time by using a reflux timer. Distilled 244 ca was neutralized by a 20 mass % aqueous potassium hydroxide solution. Recovered 244 ca (purity 100%) was 979 g (6.50 mol).

Example 1

In a two-liter four-necked flask with an agitator and a Dimroth condenser, 989.40 g of 244 ca obtained in Production Example 1 and 9.89 g of tetra-n-butylammonium chloride (TBAC) were put, and the flask was heated to 50° C. A reaction temperature was maintained at 50° C., and 1396.01 g of a 40 mass % aqueous potassium hydroxide (KOH) solution was dropped over 30 minutes. Thereafter, stirring was continued for 52 hours, and an organic layer was recovered. Note that the reaction time in this example is a total time of a time required for the above-described dropping and a time of performing the stirring after the dropping, namely, 52.5 hours.

After water washing the recovered organic layer, an analysis using the gas chromatography was carried out. The result is indicated in Table 1.

The conversion ratio described below indicates a proportion (unit: %) of a molar amount of a material (unless otherwise stated, 244 ca) consumed by the reaction to a molar amount of a material (244 ca) used for the reaction, and the selectivity means a proportion (unit: %) of a production amount (molar amount) of each of products (1233 yd(E), 1233 yd(Z), and 1-chloro-3,3-difluoropropyne) to a total amount of the products.

The yield (%) of 1233 yd(E) or 1233 yd(Z) is a numeric value in which a molar amount of products (1233 yd(E) and 1233 yd(Z)) recovered from an organic phase obtained by the reaction is indicated by a proportion (unit: %) to the molar amount of 244 ca introduced into a reaction system. "HCFO-1233 yd(E, Z) yield (%)" presented in Table 1 presents a total of yields of 1233 yd(E) and 1233 yd(Z) (other tables are also similar).

After water washing the organic layer recovered in the above, purified 1233 yd including 1233 yd(E) and 1233 yd(Z) was obtained by distillation. In the purified 1233 yd, a chlorine ion concentration was 0.14 mass ppm, a fluorine ion concentration was 0.16 mass ppm, a moisture concentration was 230 mass ppm, and an oxygen concentration was 400 ppm.

Examples 2 to 9

In the reaction device in Example 1, reactions were each performed in a process similar to that in Example 1 except to change the reactor to a three-necked or four-necked flask with an arbitrary capacity and further change reaction conditions to conditions presented in Table 1 or Table 2.

Table 1 or Table 2 presents results of a chemical composition analysis by a gas chromatogram of an organic layer obtained in each of the examples together with the conditions of the reaction and so on. Note that reaction times presented in Table 1 and Table 2 were each indicated in a unit of hour (h) obtained by rounding off a unit of minute (min).

Example 10

In the reaction device in Example 1, a reaction was performed in a process similar to that in Example 1 except to change the reactor to an autoclave made of SUS and having a capacity of 25 mL in which a pressure meter was placed and change reaction conditions to the conditions presented in Table 2. Table 2 presents a result of a chemical composition analysis by a gas chromatogram of an organic layer obtained in Example 10 together with the conditions of the reaction and so on.

Example 11

In the reaction device in Example 1, a reaction was performed in a process similar to that in Example 1 except to change the reactor to an autoclave made of Hastelloy and having a capacity of 1 L in which the pressure meter was placed and change reaction conditions to the conditions presented in Table 2. Table 2 presents a result of a chemical composition analysis by a gas chromatogram of an organic layer obtained in Example 11 together with the conditions of the reaction and so on.

TABLE 1

|  |  |  | Example 1 | | Example 2 | | Example 3 | | Example 4 | | Example 5 | |
|---|---|---|---|---|---|---|---|---|---|---|---|---|
| Reaction condition | HCFC-244ca input amount (g) | | 989.40 | | 961.96 | | 10.02 | | 9.98 | | 10.21 | |
| | Type of phase-transfer catalyst | | TBAC | | TBAC | | TBAC | | TOMAC | | TBAC | |
| | Phase-transfer catalyst use amount (Parts by mass with respect to 100 parts by mass of HCFC-244ca) | | 1 | | 1 | | 1 | | 1 | | 1 | |
| | Reaction temperature (° C.) | | 50 | | 15 | | 5 | | 50 | | 50 | |
| | Type of base | | KOH | | KOH | | KOH | | KOH | | KOH | |
| | Base concentration (mass %) in aqueous base solution | | 40 | | 40 | | 40 | | 40 | | 20 | |
| | Aqueous base solution dropping time (min) | | 30 | | 30 | | 5 | | 5 | | 5 | |
| | Aqueous base solution input amount (g) | | 1396.01 | | 1340.11 | | 9.85 | | 10.25 | | 10.49 | |
| | Molar amount of base with respect to 1 mol of HCFC-244ca | | 1.50 | | 1.50 | | 1.05 | | 1.10 | | 0.55 | |
| | Reaction time (h) | | 53 | | 62 | | 62 | | 38 | | 50 | |
| Reaction crude solution composition | GC analysis result [mass %] | Type of compound | Raw material | Reaction product | Raw material | Reaction product | Raw material | Reaction product | Raw material | Reaction product | Raw material | Reaction product |
| | | HCFC-244ca | 100.00 | 2.05 | 100.00 | 10.12 | 100.00 | 97.56 | 100.00 | 8.51 | 100.00 | 61.29 |
| | | HCFO-1233yd(E) | 0.00 | 8.37 | 0.00 | 7.66 | 0.00 | 0.21 | 0.00 | 5.13 | 0.00 | 3.04 |
| | | HCFO-1233yd(Z) | 0.00 | 89.43 | 0.00 | 82.20 | 0.00 | 2.23 | 0.00 | 86.26 | 0.00 | 35.61 |
| | | 1-chloro-3,3-difluoropropyne | 0.00 | 0.14 | 0.00 | 0.01 | 0.00 | 0.00 | 0.00 | 0.11 | 0.00 | 0.05 |
| | Organic phase recovered amount (g) | | 850.2 | | 889.4 | | 9.8 | | 9.2 | | 9.2 | |
| | HCFC-244ca conversion ratio (%) | | 98.2 | | 90.6 | | 4.8 | | 92.1 | | 44.7 | |
| | HCFO-1233yd(E) selectivity (%) | | 8.5 | | 8.5 | | 8.5 | | 5.6 | | 7.9 | |
| | HCFO-1233yd(Z) selectivity (%) | | 91.3 | | 91.5 | | 91.4 | | 94.3 | | 92.0 | |
| | 1-chloro-3,3-difluoropropyne selectivity (%) | | 0.1 | | 0.0 | | 0.0 | | 0.1 | | 0.1 | |
| | HCFO-1233yd (E, Z) yield (%) | | 96.9 | | 95.8 | | 2.7 | | 97.4 | | 40.3 | |

TABLE 2

| | | | Example 6 | | Example 7 | | Example 8 | | Example 9 | |
|---|---|---|---|---|---|---|---|---|---|---|
| Reaction condition | HCFC-244ca input amount (g) | | 9.78 | | 10.17 | | 9.93 | | 251.31 | |
| | Type of phase-transfer catalyst | | TBAC | | TBAC | | TBAC | | TBAB | |
| | Phase-transfer catalyst use amount (Parts by mass with respect to 100 parts by mass of HCFC-244ca) | | 1 | | 1 | | 1 | | 1 | |
| | Reaction temperature (° C.) | | 50 | | 50 | | 50 | | 50 | |
| | Type of base | | KOH | | NaOH | | $K_2CO_3$ | | KOH | |
| | Base concentration (mass %) in aqueous base solution | | 40 | | 40 | | 20 | | 34 | |
| | Aqueous base solution dropping time (min) | | 5 | | 5 | | 5 | | 5 | |
| | Aqueous base solution input amount (g) | | 27.30 | | 14.93 | | 49.97 | | 631.55 | |
| | Molar amount of base with respect to 1 mol of HCFC-244ca | | 2.99 | | 1.10 | | 1.10 | | 2.29 | |
| | Reaction time (h) | | 50 | | 50 | | 50 | | 30 | |
| Reaction crude solution composition | GC analysis result [mass %] | Type of compound | Raw material | Reaction product | Raw material | Reaction product | Raw material | Reaction product | Raw material | Reaction product |
| | | HCFC-244ca | 100.00 | 0.06 | 100.00 | 5.89 | 100.00 | 84.38 | 100.00 | 0.02 |
| | | HCFO-1233yd(E) | 0.00 | 8.56 | 0.00 | 7.61 | 0.00 | 1.28 | 0.00 | 8.92 |
| | | HCFO-1233yd(Z) | 0.00 | 91.25 | 0.00 | 86.38 | 0.00 | 14.34 | 0.00 | 91.02 |
| | | 1-chloro-3,3-difluoro propyne | 0.00 | 0.13 | 0.00 | 0.12 | 0.00 | 0.00 | 0.00 | 0.04 |
| Organic phase recovered amount (g) | | | 8.3 | | 9.0 | | 9.8 | | 214.2 | |
| HCFC-244ca conversion ratio (%) | | | 99.9 | | 94.8 | | 16.4 | | 100.0 | |
| HCFO-1233yd(E) selectivity (%) | | | 8.6 | | 8.1 | | 8.2 | | 8.9 | |
| HCFO-1233yd(Z) selectivity (%) | | | 91.3 | | 91.8 | | 91.8 | | 91.0 | |
| 1-chloro-3,3-difluoropropyne selectivity (%) | | | 0.1 | | 0.1 | | 0.0 | | 0.0 | |
| HCFO-1233yd (E, Z) yield (%) | | | 97.7 | | 95.9 | | 17.9 | | 98.3 | |

| | | | Example 10 | | Example 11 | |
|---|---|---|---|---|---|---|
| Reaction condition | HCFC-244ca input amount (g) | | 9.28 | | 246.06 | |
| | Type of phase-transfer catalyst | | TBAC | | TBAB | |
| | Phase-transfer catalyst use amount (Parts by mass with respect to 100 parts by mass of HCFC-244ca) | | 1 | | 1 | |
| | Reaction temperature (° C.) | | 70 | | 50 | |
| | Type of base | | KOH | | KOH | |
| | Base concentration (mass %) in aqueous base solution | | 40 | | 40 | |
| | Aqueous base solution dropping time (min) | | 5 | | 5 | |
| | Aqueous base solution input amount (g) | | 16.14 | | 530.46 | |
| | Molar amount of base with respect to 1 mol of HCFC-244ca | | 1.87 | | 2.31 | |
| | Reaction time (h) | | 88 | | 30 | |
| Reaction crude solution composition | GC analysis result [mass %] | Type of compound | Raw material | Reaction product | Raw material | Reaction product |
| | | HCFC-244ca | 100.00 | 0.09 | 100.00 | 0.01 |
| | | HCFO-1233yd(E) | 0.00 | 9.31 | 0.00 | 9.00 |
| | | HCFO-1233yd(Z) | 0.00 | 86.98 | 0.00 | 90.84 |
| | | 1-chloro-3,3-difluoro propyne | 0.00 | 3.61 | 0.00 | 0.15 |
| Organic phase recovered amount (g) | | | 4.3 | | 202.9 | |
| HCFC-244ca conversion ratio (%) | | | 100.0 | | 100.0 | |
| HCFO-1233yd(E) selectivity (%) | | | 9.5 | | 9.0 | |

TABLE 2-continued

| | | | |
|---|---|---|---|
| HCFO-1233yd(Z) selectivity (%) | | 88.8 | 90.8 |
| 1-chloro-3,3-difluoropropyne selectivity (%) | | 3.7 | 0.1 |
| HCFO-1233yd (E, Z) yield (%) | | 51.3 | 94.9 |

Examples 12 to 15

In Examples 12 to 15, in the reaction device in Example 1, the reactor was changed to the three-necked or four-necked flask with an arbitrary capacity, and water-soluble organic solvents were each used instead of using TBAC which was a phase-transfer catalyst. Reactions were each performed in a process similar to that in Example 1 except to change a type and an input amount of each of the used water-soluble organic solvents and reaction conditions other than them to conditions presented in Table 3. Table 3 presents results of a chemical composition analysis by a gas chromatogram of an organic layer obtained in each of the examples together with the conditions of the reaction and so on.

necting a gas feed line and a raw material supply line and heated to 70° C. was connected to an upper portion of the reactor.

Nitrogen, whose gas flow rate was regulated by using a mass flow controller, was supplied from the gas feed line to the raw material preheating mixing line. 244 ca which was a raw material, whose liquid flow rate was regulated by using a plunger pump, was supplied through the raw material supply line to the raw material preheating mixing line heated to 70° C. A product was continuously taken out of a lower portion of the reactor. Part of the product taken out of the lower portion of the reactor was picked, and a chemical composition analysis was performed by the gas chromatography (GC). Hereinafter, the product taken out of the lower portion of the reactor is referred to as an outlet gas.

TABLE 3

| | | | Example 12 | | Example 13 | | Example 14 | | Example 15 | |
|---|---|---|---|---|---|---|---|---|---|---|
| Reaction condition | HCFC-244ca input amount (g) | | 10.05 | | 10.01 | | 10.27 | | 10.25 | |
| | Type of water-soluble organic solvent | | Tetraethylene glycol dimethyl ether | | Tetraethylene glycol dimethyl ether | | Sulfolane | | t-butanol | |
| | Water-soluble organic solvent use amount (Parts by mass with respect to 100 parts by mass of HCFC-244ca) | | 50 | | 100 | | 100 | | 100 | |
| | Reaction temperature (° C.) | | 50 | | 50 | | 50 | | 50 | |
| | Type of base | | KOH | | KOH | | KOH | | KOH | |
| | Base concentration (mass %) in aqueous base solution | | 40 | | 40 | | 40 | | 40 | |
| | Aqueous base solution dropping time (min) | | 5 | | 5 | | 5 | | 5 | |
| | Aqueous base solution input amount (g) | | 10.42 | | 10.90 | | 10.80 | | 10.78 | |
| | Molar amount of base with respect to 1 mol of HCFC-244ca | | 1.11 | | 1.17 | | 1.13 | | 1.13 | |
| | Reaction time (h) | | 30 | | 30 | | 30 | | 30 | |
| Reaction crude solution composition | GC analysis result [mass %] | Type of compound | Raw material | Reaction product | Raw material | Reaction product | Raw material | Reaction product | Raw material | Reaction product |
| | | HCFC-244ca | 100.00 | 72.85 | 100.00 | 68.86 | 100.00 | 31.71 | 100.00 | 35.68 |
| | | HCFO-1233yd(E) | 0.00 | 2.23 | 0.00 | 2.83 | 0.00 | 5.61 | 0.00 | 0.19 |
| | | HCFO-1233yd(Z) | 0.00 | 24.91 | 0.00 | 28.29 | 0.00 | 62.67 | 0.00 | 64.12 |
| | | 1-chloro-3,3-difluoropropyne | 0.00 | 0.01 | 0.00 | 0.01 | 0.00 | 0.01 | 0.00 | 0.00 |
| | Organic phase recovered amount (g) | | 9.9 | | 9.9 | | 10.2 | | 10.1 | |
| | HCFC-244ca conversion ratio (%) | | 28.4 | | 31.8 | | 68.6 | | 64.7 | |
| | HCFO-1233yd(E) selectivity (%) | | 8.2 | | 9.1 | | 8.2 | | 0.3 | |
| | HCFO-1233yd(Z) selectivity (%) | | 91.8 | | 90.9 | | 91.8 | | 99.7 | |
| | 1-chloro-3,3-difluoropropyne selectivity (%) | | 0.0 | | 0.0 | | 0.0 | | 0.0 | |
| | HCFO-1233yd (E, Z) yield (%) | | 30.8 | | 35.6 | | 77.9 | | 73.3 | |

Comparative Example 1

An insertion tube (material: SUS316, diameter: 3 mm) was introduced into the center of a vertical fixed-bed reactor (material: SUS316, 22.0 mm in inside diameter×200 mm in height), a K-type thermocouple was inserted therein, and an internal temperature was measured. The center portion of the reactor was filled with 83.0 mL (43.0 g) of an activated carbon (manufactured by Japan EnviroChemicals, Limited, SHIRASAGI activated carbon CMX), which was set as a catalyst layer. The catalyst layer was heated to 100° C. and dried by an electric furnace while supplying nitrogen gas at 300 mL/min. A raw material preheating mixing line con- Nitrogen and the raw material were introduced into the reactor under conditions presented in Table 4 and made to react with each other continuously for three hours. Part of the outlet gas was picked immediately before a reaction completion, and the chemical composition analysis was performed by the gas chromatography (GC). Table 4 presents a result.

Comparative Examples 2 to 4

A vertical fixed-bed reactor (material: SUS316, 22.6 mm in inside diameter×200 mm in height) was used as a reactor and alumina (manufactured by JGC Catalysts and Chemicals Ltd., N612N) was used as a catalyst, and the catalyst was dried at 300° C. in a process similar to that in Comparative Example 1. Thereafter, chlorodifluoromethane (HFC-22)

was supplied at 300 mL/min, and the catalyst was activated for about ten hours until a composition of the outlet gas was stabilized. Reactions were each performed in a process similar to that in Comparative Example 1 except to change a reaction temperature and reaction conditions other than it to conditions presented in Table 4. Table 4 presents the reaction conditions and results.

TABLE 4

|  |  | Comparative Example 1 | | Comparative Example 2 | | Comparative Example 3 | | Comparative Example 4 | |
|---|---|---|---|---|---|---|---|---|---|
| Reaction condition | Catalyst | Activated carbon | | $Al_2O_3$ | | $Al_2O_3$ | | $Al_2O_3$ | |
|  | Reaction temperature (° C.) | 350.0 | | 350.0 | | 450.0 | | 500.0 | |
|  | Reaction pressure (MPa (gage)) | 0 | | 0 | | 0 | | 0 | |
|  | Contact time (sec) | 20 | | 20 | | 20 | | 20 | |
|  | Linear velocity (cm/sec) | 1 | | 1 | | 1 | | 1 | |
|  | $N_2$ flow rate (Nml/min) | 49.0 | | 52.0 | | 45.0 | | 42.0 | |
|  | 244ca flow rate (Nml/min) | 49.0 | | 52.0 | | 45.0 | | 42.0 | |
| Reaction crude solution composition | GC analysis result [mass %] | Type of compound | Raw material | Reaction product | Raw material | Reaction product | Raw material | Reaction product | Raw material | Reaction product |
|  |  | HCFC-244ca | 100.000 | 99.211 | 99.911 | 98.800 | 99.911 | 94.900 | 99.911 | 97.924 |
|  |  | HCFO-1233yd(E) | 0.000 | 0.030 | 0.000 | 0.000 | 0.000 | 0.000 | 0.000 | 0.000 |
|  |  | HCFO-1233yd(Z) | 0.000 | 0.125 | 0.000 | 0.016 | 0.000 | 0.016 | 0.000 | 0.016 |
|  |  | 1-chloro-3,3-difluoropropyne | 0.000 | 0.000 | 0.000 | 0.030 | 0.000 | 0.069 | 0.000 | 0.022 |
|  |  | Others | 0.000 | 0.635 | 0.089 | 1.154 | 0.089 | 5.015 | 0.089 | 2.037 |
|  | HCFC-244ca conversion ratio (%) | 0.79 | | 1.11 | | 5.02 | | 1.99 | |
|  | HCFO-1233yd(E) selectivity (%) | 0.04 | | 0.00 | | 0.00 | | 0.00 | |
|  | HCFO-1233yd(Z) selectivity (%) | 0.16 | | 0.05 | | 0.02 | | 0.03 | |
|  | 1-chloro-3,3-difluoropropyne selectivity (%) | 0.00 | | 3.71 | | 7.34 | | 3.17 | |
|  | HCFO-1233yd (E, Z) yield (%) | 0.04 | | 0.001 | | 0.001 | | 0.0005 | |

What is claimed is:

1. A method of manufacturing 1-chloro-2,3,3-trifluoropropene, comprising;
   subjecting 3-chloro-1,1,2,2-tetrafluoropropane to a dehydrofluorination reaction in a liquid phase in the presence of a base and a solvent, and a proportion of mass of the base to a total mass of the solvent and the base is 0.5 to 40 mass %.

2. The method of manufacturing 1-chloro-2,3,3-trifluoropropene according to claim 1, wherein the base is at least one selected from the group consisting of a metal hydroxide, a metal oxide, and a metal carbonate.

3. The method of manufacturing 1-chloro-2,3,3-trifluoropropene according to claim 1, wherein the base is a metal hydroxide.

4. The method of manufacturing 1-chloro-2,3,3-trifluoropropene according to claim 1, wherein the base is at least one selected from the group consisting of potassium hydroxide and sodium hydroxide.

5. The method of manufacturing 1-chloro-2,3,3-trifluoropropene according to claim 1, wherein an amount of the base is 0.5 to 10.0 mol with respect to 1 mol of the 3-chloro-1,1,2,2-tetrafluoropropane.

6. The method of manufacturing 1-chloro-2,3,3-trifluoropropene according to claim 1, wherein the dehydrofluorination reaction is performed at a reaction temperature of 5 to 80° C.

7. The method of manufacturing 1-chloro-2,3,3-trifluoropropene according to claim 1, wherein the solvent is water.

8. The method of manufacturing 1-chloro-2,3,3-trifluoropropene according to claim 1, wherein the dehydrofluorination reaction is performed in the presence of a phase-transfer catalyst.

9. The method of manufacturing 1-chloro-2,3,3-trifluoropropene according to claim 8, wherein the phase-transfer catalyst is a quaternary ammonium salt.

10. The method of manufacturing 1-chloro-2,3,3-trifluoropropene according to claim 9, wherein the quaternary ammonium salt is at least one selected from the group consisting of tetra-n-butylammonium chloride, tetra-n-butylammonium bromide, and methyltri-n-octylammonium chloride.

11. The method of manufacturing 1-chloro-2,3,3-trifluoropropene according to claim 1, wherein the dehydrofluorination reaction is performed in the presence of a water-soluble organic solvent capable of dissolving the 3-chloro-1,1,2,2-tetrafluoropropane.

12. The method of manufacturing 1-chloro-2,3,3-trifluoropropene according to claim 11, wherein the water-soluble organic solvent is used in a proportion of 1 to 200 parts by mass to 100 parts by mass of the 3-chloro-1,1,2,2-tetrafluoropropane.

13. The method of manufacturing 1-chloro-2,3,3-trilluoropropene according to claim 1, wherein the dehydrofluorination reaction is conducted for a time of 62 hours or less.

14. The method of manufacturing 1-chloro-2,3,3-trifluoropropene according to claim 1, wherein the dehydrofluorination reaction is performed at a reaction temperature of 5 to 60° C.

* * * * *